United States Patent [19]

Ogilvie

[11] Patent Number: 4,460,690

[45] Date of Patent: Jul. 17, 1984

[54] STIMULATION OF VIRAL GROWTH RATE

[75] Inventor: Kelvin K. Ogilvie, Candiac, Canada

[73] Assignee: ens Bio Logicals inc., Toronto, Canada

[21] Appl. No.: 467,900

[22] Filed: Feb. 18, 1983

[51] Int. Cl.³ .................... C12N 7/00; C07D 473/00
[52] U.S. Cl. ................................. 435/235; 544/276
[58] Field of Search ................ 544/276; 424/253; 435/235

[56] References Cited

U.S. PATENT DOCUMENTS 4,347,360  8/1982  Ogilvie .......................... 544/276

Primary Examiner—Sam Rosen
Attorney, Agent, or Firm—Murray, Whisenhunt & Ferguson

[57] ABSTRACT

The novel nucleoside analogue 9-[1-(1,3-diacetoxy-2-propoxy)-2-acetoxy]ethylguanine has the effect of stimulating the rate of growth of certain viruses, particularly influenza viruses, so that culturing virally infected cells in the presence of this compound substantially decreases the time required for diagnosis and typing of the virus, ready for administration of appropriate anti viral measures.

4 Claims, No Drawings

STIMULATION OF VIRAL GROWTH RATE

FIELD OF THE INVENTION

This invention relates to nucleoside analogue compounds, and more particulary to compounds which have an effect on the growth and replication of viruses such as influenza viruses in mammalian cells.

BACKGROUND OF THE INVENTION

Influenza viruses which infect mammals are of many different types and strains. Whilst drugs and vaccines are available for the prevention of influenze infection and the control or cure of the infection after contraction, many of these drugs and vaccines are highly selective in their action, and are only effective against a specific type of influenza virus. Consequently, before a cure for the infection can be prescribed, and before an effective preventive vaccine can be administered to control the spread of an influenza virus infection, the type of influenza virus responsible must be identified. The time required to cultivate and type the virus is considerable, and may require from one to several weeks. When outbreaks of the disease occur in communities, this time required for diagnosis is a serious handicap in attempting to control the spread of the disease. There is accordingly a need for a means which will make significant reductions in the time required for influenza virus diagnosis.

SUMMARY OF THE INVENTION

The present invention alleviates this problem, by providing a novel chemical compound, namely a nucleoside analogue, which stimulates the growth of influenza and similar viruses. The novel compound if 9-[1-(1,3-diacetoxy-2-propoxy)-2-acetoxy]ethylguanine, of structural formula:

(I)

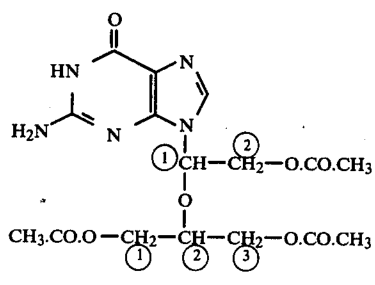

(circled numbers indicating the carbon atom numbering in the above nomenclature system for the compound). The use of this compound in the medium in which influenza virus-infected cells are grown causes an increase of viral growth of as much as 200%, thereby materially reducing the time required for cultivation and diagnosis of the influenza virus type. The compound also has a stimulative effect on the growth of coxsackievirus, specifically CVB 3.

DESCRIPTION OF THE PREFERRED EMBODIMENTS

Compound I can be prepared from the corresponding tri-hydroxyl compound, of formula:

(II)

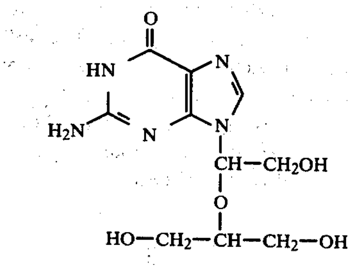

which is a known compound, being shown in "Biochemical Pharmacology" Vol. 30, No. 22, pages 3071-3077, 1981, an article by Keller et al entitled "Enzymatic Phosphorylation of Acyclic Nucleoside Analogues and Correlations with Antiherpetic Activities" (see compound no. 12, page 3073). Compound II may be made from guanosine, by oxidation in a first step to cleave the sugar ring between the carbon 2′ and 3′ and form a dialdehyde, followed by reduction thereof to the trialcohol (II). Acetylation of compound II to compound I is accomplished by reaction with acetic anhydride or the like, in a normal way.

In use, the compound I is employed in in vitro testing, whereby cells infected with the virus under test are incubated in a suitable nutrient medium and under growth promoting conditions, in the presence of a suitable amount of compound I. Relatively small amounts of compound I can be used. For example, amounts in the range of 0.01-1 milligrams of compound per milliliter of culture medium are generally effective in providing the necessary growth stimulation. Once the virally infected cells have been grown to the required extent, they can be recovered and the virus typed and classified by standard, known procedures.

It will of course be understood that references herein to the compound 9-[1-(1,3-diacetoxy-2-propoxy)-2-acetoxy]ethylguanine also include its acid addition salts, which have essentially the same activity towards the viruses.

The invention is further described in the following, non-limiting examples.

EXAMPLE 1

The compound 9-[1-(1,3-diacetoxy-2-propoxy)-2-acetoxy]ethylguanine (I) was synthesized by a three step procedure from guanosine.

2.5 g of guanosine were suspended in 300 ml of water. 2.5 g of sodium periodate $NaIO_4$ were added in small portions to the solution under stirring and under protection from light. The mixture was kept for 18 hours. The solution was clear. The dialdehyde so formed was not isolated, but was reacted in the same solution to reduce it to the corresponding alcohol. Thus, 4 g of sodium borohydride $NaBH_4$ were added in small portions under stirring, and the solution kept overnight. The following day, the solution was acidified with glacial acetic acid and evaporated under vacuum to dryness. The evaporation was repeated several times with water and methanol to remove boric acid. After drying on a vacuum overnight, the white solid was treated with 30 ml of dry DMF, 30 ml of dry pyridine and 30 ml of acetic anhydride. The mixture was stirred at room temperature for 24 hours. The insoluble material was filtered. The residue was washed with methylene chloride. The filtrate and washing solution were combined and added to 50 ml of methanol to destroy excess acetic anhydride. The solution was evaporated to dryness. The residue was extracted with methylene chloride, washed with water and dried over magnesium sulphate. The solvent was removed under vacuum, the residue was subjected to chromatography on silica gel, with methylene chloride:methanol in a 9:1 ratio as eluant. A yield of 2 g (about 55%) of desired product was obtained. Melting point 192°–194° C. $1_H$-NMR ($DMSOd_6$):

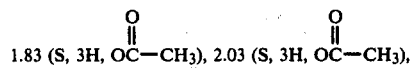

$$1.83\ (S,\ 3H,\ O\overset{\overset{O}{\|}}{C}-CH_3),\ 2.03\ (S,\ 3H,\ O\overset{\overset{O}{\|}}{C}-CH_3),$$

$$2.13\ (S,\ 3H,\ O\overset{\overset{O}{\|}}{C}-CH_3)$$

EXAMPLE 2

Compound I was subjected to in vitro testing, to demonstrate its activity against influenza virus A. A viral plaque assay method is used for this purpose.

Madden Darby Canine Kidney (MDCK) cells were routinely grown and maintained in Basal Medium Eagle (BME) supplemented with 10% fetal calf serum, 0.112% sodium bicarbonate, 2 mM L-glutamine, 2 mg% Neomycin.

Before and during the tests, cells are run in 6-well Linbro plates (plastic) in BME and incubated at 37° C. in a 5% carbon dioxide atmosphere until 90% confluent.

MDCK cell monolayers are rinsed twice with phosphate buffered saline (PBS) and inoculated with 0.2 ml of a working dilution of each stock influenza A/NWS/33 virus calculated to yield 75–100 plaque forming units per well, or sham inoculated with 0.2 ml of PBS diluent. Monolayers are incubated at ambient temperature with intermittent agitation for 1 hour.

Monolayers are aspirated when overlayed with two ml of Agar overlay medium, with or without drug under test. The plates are incubated at 34° C. in 5% carbon dioxide for three days.

On the third day, Cornoy's solution is added directly to each Agar overlay in order to fix monolayers to each well.

Agar overlays are removed and discarded, and each monolayer is stained with 1% crystal violet in 50% ethanol at ambient temperatures for 30 minutes. The stain is removed and wells are rinsed with PBS and drained. The plaque numbers are counted directly, and the mean plaque area is calculated.

It was found that compound I in an amount of 200 micrograms per ml, caused a 200% increase in numbers of plaques, as well as an increase in their size.

I claim:

1. 9-[1-(1,3-diacetoxy-2-propoxy)-2-acetoxy]ethylguanine, or acid addition salts thereof.

2. 9-[1-(1,3-diacetoxy-2-propoxy)-2-acetoxy]ethylguanine.

3. A process of stimulating the growth and replication of viruses including influenza A virus and coxsackievirus CVB 3, which comprises incubating mammalian cells infected with said virus in a growth promoting medium and under growth promoting conditions, said medium including an effective amount of 9-[1-(1,3-diacetoxy-2-propoxy)-2-acetoxy]ethylguanine or an acid addition salt thereof.

4. A process of making 9-[1-(1,3-diacetoxy-2-propoxy)-2-acetoxy]ethylguanine, which comprises reacting 9-[1-(1,3-dihydroxy-2-propoxy)-2-hydroxy]ethylguanine with an acetylating reagent selected from acetic anhydride or an acetyl halide.

* * * * *